US006410754B1

(12) United States Patent
Soula et al.

(10) Patent No.: US 6,410,754 B1
(45) Date of Patent: *Jun. 25, 2002

(54) PHOTOCHROMIC SPIROPYRANS, AND COMPOSITIONS AND ARTICLES CONTAINING SAME

(75) Inventors: Gérard Soula, Meyzieu; You-Ping Chan, Lyons, both of (FR)

(73) Assignee: Flamel Technologies, Venissieux (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/913,620

(22) PCT Filed: Mar. 21, 1996

(86) PCT No.: PCT/FR96/00429

§ 371 (c)(1),
(2), (4) Date: Nov. 14, 1997

(87) PCT Pub. No.: WO95/03739

PCT Pub. Date: Oct. 3, 1996

(30) Foreign Application Priority Data

Mar. 24, 1995 (FR) .............................. 95 03739

(51) Int. Cl.[7] .................. C07D 241/36; C07D 213/22; C07D 311/96
(52) U.S. Cl. ................ 549/331; 549/381; 549/456; 549/472; 549/473; 546/258; 544/344; 525/420; 525/437; 525/450; 525/452; 525/461
(58) Field of Search ................ 549/331, 381, 549/456, 472, 473; 544/344; 546/258

(56) References Cited

U.S. PATENT DOCUMENTS 5,395,567 A  3/1995  Van Gemert et al. ....... 252/586

FOREIGN PATENT DOCUMENTS

| EP | 0 401 958 | 12/1990 |
| EP | 0 562 915 | 9/1993 |
| EP | 0 625 518 | 11/1994 |
| WO | 93/10112 | 5/1993 |
| WO | 95/00504 | 1/1995 |
| WO | 95/05382 | 2/1995 |

OTHER PUBLICATIONS

Malkin et al., *J. Photochem. Photobiol.*, 49:1–2, 1989, 75–78.

Malkin et al., *Izv. Akad. Nauk SSSR, Ser. Khim.*, 39:2, 1990, 236–242.

Krasieva et al., *Izv. Akad. SSSR, Ser. Khim.*, 38:11, 2297–2302.

Aldoshin et al., *Izv. Akad. Nauk SSSR, Ser. Khim.*, 37:7, 1988, 1385–1387.

*Primary Examiner*—Floyd D. Higel
*Assistant Examiner*—Ebenezer Sackey
(74) *Attorney, Agent, or Firm*—James C. Lydon

(57) ABSTRACT

Novel spiropyran compounds, particularly with photochromic properties, are disclosed, as well as photochromic compositions and ophthalmic articles containing said compounds. The photochromes have been designed so as to have a high colorability, a high sensitivity to activating radiation breaking the pyran ring, to be entirely or practically free from coloration in a non activated non exposed state, to have an intense coloration following activation and a high coverage of the visible spectrum in combination with at least one other photochrome, and to have high rates of coloration/decoloration. The spiropyrans are easily produced and photochemically stable, and are, e.g., of formula (i), wherein L=(a); (b).

38 Claims, No Drawings

PHOTOCHROMIC SPIROPYRANS, AND COMPOSITIONS AND ARTICLES CONTAINING SAME

This application is a 371 of PCT/FR96/00429 field Mar. 21, 1996.

TECHNICAL FIELD

The present invention relates to novel compounds of the spiropyran type which have photochromic properties in particular. It further relates to the photochromic compositions and ophthalmic articles (e.g. lenses) containing these spiropyrans.

PRIOR ART

Photochromic compounds are capable of changing color under the influence of polychromatic or monochromatic light (e.g. UV) and of reverting to their initial color when the light irradiation ceases, or under the influence of a different polychromatic or monochromatic light from the first, or under the influence of temperature and/or a different polychromatic or monochromatic light from the first.

These photochromic compounds have applications in a variety of fields, for example for the manufacture of ophthalmic lenses, contact lenses, sunglasses, filters, lenses for moving or still cameras or for other optical and observation devices, glazing, decorative objects or display elements, or alternatively for the storage of information by optical recording (coding).

In the field of ophthalmic optics and particularly glasses, a photochromic lens comprising one or more photochromic compounds must have, over a wide temperature range (−20° C. to +50° C.), a high transmission in the dark or in the absence of sunlight, a low transmission (high colorability) under solar irradiation, fast coloration and decolorization kinetics, an appreciable durability with an optimal efficacy, and a pleasant tint acceptable to-the consumer (preferably gray or brown).

These lens characteristics are in fact determined by the active photochromic compounds, which must also be perfectly compatible with the organic or inorganic substrate of which the lens is made. It should furthermore be noted that, to obtain a gray or brown tint, it may be necessary to use at least two photochromic compounds of different colors, i.e. with different maximum absorption wavelengths in the visible ($\lambda_{max}$). This association also makes other demands on the photochromic compounds. In particular, the coloration and decolorization kinetics of the two types of active photochromic compounds in association must be substantially identical. The same applies to their stability over time and also to their compatibility with a plastic or inorganic substrate.

The benzopyrans and naphthopyrans forming the subject of the invention according to U.S. Pat. No. 3,567,605 may be mentioned among the numerous photochromic compounds described in the prior art. When subjected to temperatures of the order of −30 or −40° C., these compounds change from a colorless state to a yellow-orange or even red tint under high energy activating irradiation of the UV type. These compounds revert to the colorless state when the temperature is raised ($\geq$0° C.) and/or when they are irradiated in the visible. The thermal and kinetic conditions of the photochromism peculiar to these compounds seem a priori to be rather incompatible with common ophthalmic applications.

These compounds also have relatively low $\lambda_{max}$ values in the visible.

In the case of photochromic compounds of the pyran type, high energy radiation (UV) allows the opening of the pyran ring and hence the conjugation of double bonds. This ring opening causes the appearance of an absorbance in the visible whose $\lambda_{max}$, colorability Ao and $\lambda_{max}$ peak height and area are characteristic.

Patent application EP 0 562 915 discloses novel heterocyclic chromenes which are useful as photochromic compounds in the field of ophthalmic optics. These compounds are benzopyrans or chromenes substituted by two phenyls, which themselves are optionally substituted. These photochromic compounds are presented as having a colorability in the red region ($\lambda_{max}$=438–510 nm) and as being usable with photochromic compounds whose $\lambda_{max}$ is situated in the blue ($\approx$600 nm). It has been found, however, that these known compounds are still capable of improvement as regards their colorability and their photochemical stability.

More recently, U.S. Pat. No. 5,238,281 has disclosed novel photochromic compounds of the naphthopyran type substituted in the 5-, 8- and 9-positions of the naphthyl moiety. According to the assignee, these substitutions, and more particularly the one in the 8-position of a naphthopyran which is itself substituted in the 3-position by two phenyl groups, effects an increase in the photochromic sensitivity, said increase supposedly being related to a bathochromic modification of the activating UV spectrum. This specific substitution of the naphthyl is also said to be the cause of a bathochromic change in the visible absorption spectrum of the activated compound (exposed to UV). The two phenyl substituents on the pyran ring are structurally independent. The $\lambda_{max}$ values in the visible of the photochromic compounds according to this US patent range from 432 nm to 543 nm.

Despite all these improvements, these naphthopyrans have the disadvantage of possessing an insufficient colorability and a $\lambda_{max}$ (visible) which is rather incompatible with the most commonly available complementary photochromic compounds for obtaining satisfactory tints and colorabilities.

Furthermore, patent applications WO 95/00 504 and WO-A-95/05 382 and U.S. Pat. No. 5,395,567 describe diphenylnaphthopyrans or diphenylheterobenzopyrans in which the two phenyl radicals, bonded to the 2-position of the pyran ring, are bridged by a direct a bond or the following groups:

In WO 95/00 504 the bridging is proposed in order to reduce the rate of diffusion of these products in a polymeric matrix.

The products in which the bridging is formed by a direct bond are photochemically unstable. Those with the following bridging:

have a low colorability.

In this state of the art, one of the essential objects of the present invention is to provide novel compounds, particularly photochromic compounds, which belong to the spiropyran family and do not exhibit the disadvantages of the known photochromic compounds of the same type. In particular, the invention relates to spiropyrans possessing:

a high colorability, a high sensitivity to the activating irradiation which causes the opening of the pyran ring (, e.g. in the UV with large peak height and area), an absence of coloration or a very weak coloration in the non-activated (non-exposed) state, an intense coloration after activation: large peak height and area at $\lambda_{max}$ in the visible, $\lambda_{max}$ in the visible which, in association with at least one other photochromic compound of complementary $\lambda_{max}$. in the visible, permits a substantial coverage of the visible spectrum, high coloration/decolorization rates, suitability for photochromism over a wide and extensive temperature range (−20° C. to +50° C.), long durability (of the optimal efficacy), it also being necessary for these spiropyrans to be easy to prepare.

Another object of the invention relates to the use of the photochromic compounds in the field of ophthalmic optics and particularly for their use in and/or on ophthalmic lenses, i.e., in terms of the invention, lenses for glasses (sunglasses), contact lenses and lenses for optical devices, inter alia.

Within the framework of the use of the above-mentioned photochromic compounds, another object of the invention is to provide compositions which comprise said photochromic compounds and are intended for example for use in the coating of ophthalmic lenses or as constituent chromogenic agents of said lenses.

Another object of the invention is to provide the photochromic compound in the form of polymers and/or crosslinking agents.

Another object of the invention is to provide an organic polymeric or copolymeric matrix and/or an inorganic matrix containing the above-mentioned photochromic compounds in polymeric or non-polymeric form.

Another object of the invention relates to the ophthalmic articles, for example of the lens type (e.g. lenses for sunglasses), glazing, glazing elements, optical components, sensors, and devices for coding, storing or displaying information which contain the above-mentioned photochromic compounds in polymeric or non-polymeric form, and/or the compositions comprising them, and/or the organic polymeric matrices or the inorganic matrices including these compounds and/or compositions.

BRIEF DISCLOSURE OF THE INVENTION

To achieve these and other objects, it is to the Applicant's credit to have demonstrated, after numerous studies and experiments, that, totally surprisingly and unexpectedly, it is necessary to select, from spiropyrans substituted on $C_2$ by two aromatic or heteroaromatic radicals chemically bonded to one another, certain specific compounds characterized by the nature of this chemical bond. DETAILED DESCRIPTION OF THE INVENTION:

Thus the present invention relates to a compound, particularly a photochromic compound, of the following general formula (I):

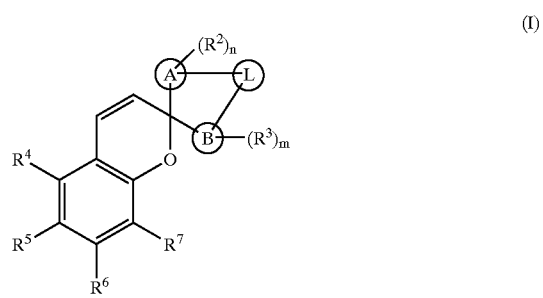

in which:
$R^2, R^3, R^4, R^5, R^6$ and $R^7$ are identical or different and are:
  hydrogen, U an alkyl, cycloalkyl, alkenyl, alkynyl, aryl or heteroaryl group (preferably phenyl or naphthyl mono-, di- or tri-substituted by donor or acceptor groups) or an aryloxy or aralkyl group, said group optionally being halogenated,
  a halogen, preferably F, Br or Cl,
  OR, SR, —OCOR or —COOR, where R—H, alkyl and/or cycloalkyl and/or aryl,
  a (poly)ether, a (poly)amide, a (poly)carbonate, a (poly)carbamate, a (poly)urea or a (poly)ester,
    an amino radical which—once bonded in (I)—produces a primary, secondary or tertiary amine, said amine being monosubstituted or disubstituted by alkyl, aryl or aralkyl, depending on its type,
    or a cyclic amino radical optionally containing one or more heteroatoms,
  or an electron-attracting group preferably selected from the group comprising $CF_3$, CN, $NO_2$ and SCN,
at least two of the radicals $R^4$, $R^5$, $R^6$ and $R^7$, preferably carried by two vicinal carbons, can optionally form at least one aromatic or aliphatic ring advantageously having from 4 to 7 ring members and even more advantageously having five or six ring members, said ring(s) optionally comprising at least one heteroatom so as to form at least one heterocyclic ring, the latter ring(s) optionally being substituted by one or more identical or different radicals defined as above for $R^2$ to $R^7$,
n and m independently of one another take the values 0 to 4, and it being possible, when n and/or m≧2, for two of the radicals $R^2$ or $R^3$ optionally to combine to form at least one aromatic ring,
a bonding unit L is provided between two moieties A and B consisting of aromatic or heteroaromatic rings (A and B being identical or different), and
L is preferably joined to the 2,2'-positions of the rings A and B, said formula (d) being characterized in that L is selected from the following group of radicals:

where:
$R^8$ and $R^9$ are identical or different and are a linear or branched $C_1$–$C_{12}$ alkyl, a $C_1$–$C_{12}$ cycloalkyl, an aryl, an aralkyl or an alkylaryl, these radicals $R^8$ and $R^9$ being:
  optionally substituted,
  and preferably selected from the following group of radicals: alkylene, phenyl and/or alkyl, methyl and methylenephenyl radicals being particularly preferred, $R^8$ and $R^9$ can optionally combine to form a substituted or unsubstituted hydrocarbon ring which may or may not be fused with at least one aromatic and/or aliphatic ring optionally containing at least one heteroatom, this ring preferably being aliphatic and having from 4 to 7 ring members, and x=1 to 3.

Contrary to all expectations, joining the two (hetero) aromatic rings A and B by an appropriate chemical bond to the carbon in the $C_2$-position of the pyran ring did not have negative repercussions on the photochromicity properties of the compound. On the contrary, it was possible to identify a substantial improvement in all the photochromic characteristics of the compounds, especially the colorability and the $\lambda_{max}$ in the visible (widening of the $\lambda_{max}$ range).

According to a preferred modality of the invention, the two aromatic rings A and/or B are phenyls joined to one another by the bonding unit L, which is connected to their respective carbons in the 2- and 2'-positions. This corresponds to the following general formula (I'):

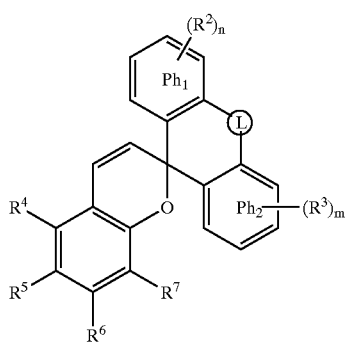

in which $R^2$ to $R^7$, n and m are as defined above.

This novel family of spiropyrans is characterized by the presence of two rings, respectively pyran and hydrocarbon rings, joined by the spiro carbon. The choice of specific bonding units L for these spiropyrans affords very good compromises as regards the combination of photochromic properties and photochemical stability. In particular, these bridged spiropyrans have a better colorability and their photocoloration band experiences a bathochromic shift relative to the analogous known compounds.

Moreover, the products according to the invention have photocoloration and decolorization kinetics adapted to the intended applications.

Among the substituents which can be considered for the compounds of formulae (I) and (I') according to the invention, it is appropriate to consider groups $R^2$ to $R^7$ comprising and/or forming at least one reactive polymerizing and/or crosslinking group preferably selected from the following list: alkenyl, advantageously vinyl, methacryloyl, acryloyl, acryloxyalkyl, methacryloxyalkyl or epoxy.

Thus the photochromic compounds according to the invention can be thought of as monomers of identical or different type which are capable of reacting with one another or with other comonomers to form homopolymers and/or copolymers carrying a photochromic functional group and possessing mechanical properties of macromolecules. It follows that one of the subjects of the present invention is formed by these homopolymers or copolymers comprising (co)monomers, and/or by crosslinked products at least partially consisting of photochromic compounds (I), (I') according to the invention.

Similarly the above-mentioned compounds (I), (I') can be thought of as crosslinking agents provided with reactive groups capable of creating bridges between polymer chains of photochromic or non-photochromic type. The crosslinked products which can be obtained in this way also constitute a further subject of the present invention.

In the structural variant referred to above, according to which at least two of the radicals $R^4$ to $R^7$ form a cyclic structure, preference is readily given (but without implying a limitation) to the cyclization of $R^4-R^5$ to give, in combination with a grouping shared with the benzyl of the benzopyranyl unit, one of the following rings: phenyl, pyridyl, thienyl, furyl, piperidinyl or furfuryl.

The more particularly preferred ring $R^4-R^5$ is:
either a phenyl, the compound obtained thus being a naphthospiropyran,
or a heterocycle, advantageously of the type containing oxygen as the heteroatom, preference being given to tetrahydrofuran rings optionally fused with a phenyl ring.

In the latter case, the preferred compound obtained is a heterobenzopyran.

Specific examples which may be mentioned of some of the interesting structures of the compounds of formulae (I) and (I'), without implying a limitation, are those in which:
$R^2$ and $R^3$ are hydrogen or —OMe,
and at least two radicals $R^4$ and $R^5$ or $R^6$ and $R^7$ form a ring selected
from the following group:

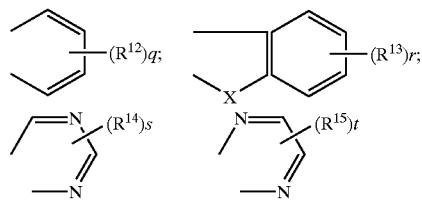

where $R^{12}$ to $R^{15}$ are defined as above for $R^2$ to $R^7$, q, r and s=0 to 4 and t=0 to 2,
and X=O, S or N,
and even more preferably from the following subgroup:

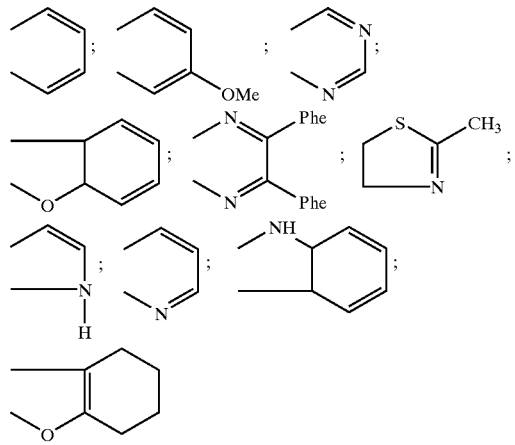

In general terms, the following designations according to the invention apply to the foregoing formulae:
"alkyl" is preferably an optionally unsaturated, linear or branched hydrocarbon group having from 1 to 10 carbon atoms (alkenyl, alkynyl),
"cycloalkyl" is a monocyclic or polycyclic hydrocarbon group preferably having from 3 to 10 carbon atoms,
"alkoxy" is a group of the —O—alkyl type preferably having from 1 to 10 carbon atoms,
"aryl" is an aromatic hydrocarbon group comprising at least 5 carbon atoms, "heteroatyl" is an aromatic hydrocarbon group comprising at least 5 atoms, at least one of which is a heteroatom, "aralkyl" is a group comprising at least one alkyl and at least one aryl, as defined above, "heteroatom" is an atom other than C and H and preferably belonging to the following group: N, O, S, P, F, Cl, Br.

As is apparent from the above, the photochromic compounds which are more readily used within the framework of the invention are therefore naphtho-spiropyrans or heterobenzopyrans:

- optionally substituted in the $C_8$-position of the naphthopyran ring by an alkoxy, preferably a methoxy,
- and/or optionally carrying an alkoxy group, preferably a methoxy group, on at least one of the phenyls of the spiro carbon.

The following may be mentioned among the most advantageous spiropyrans:

(A)
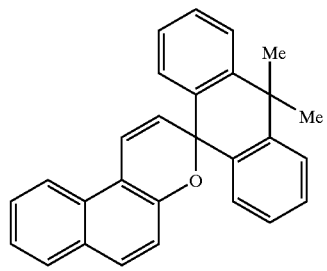

(B)
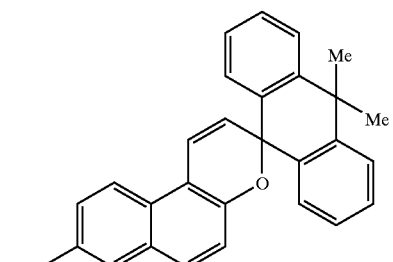

(C)
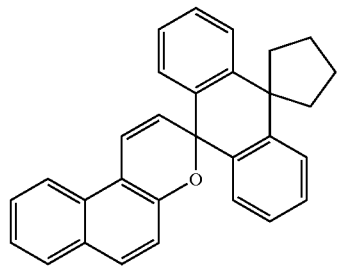

(D)
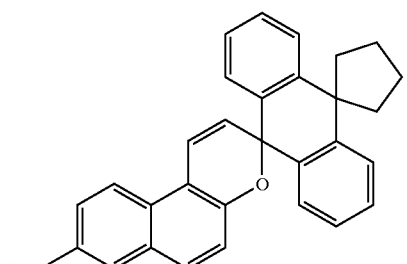

(E)
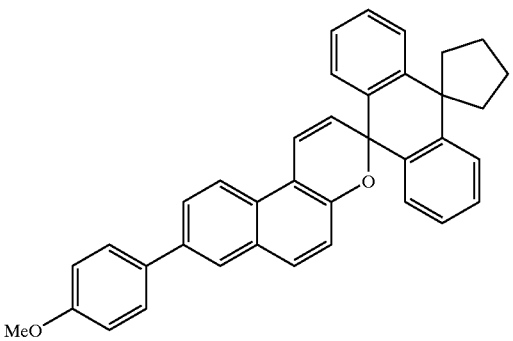

(F)
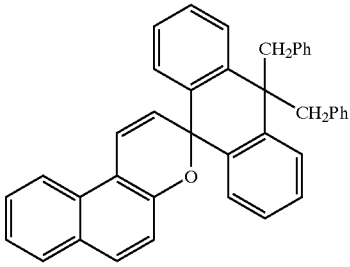

(G)
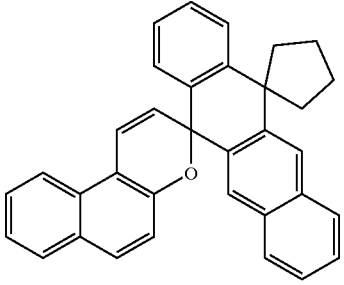

(H)
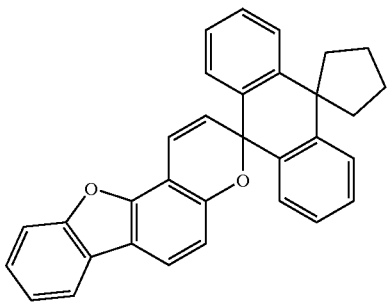

(I)
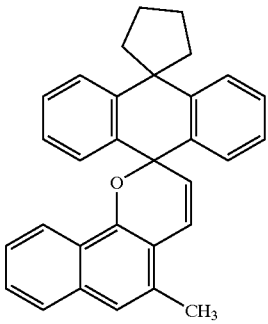

-continued

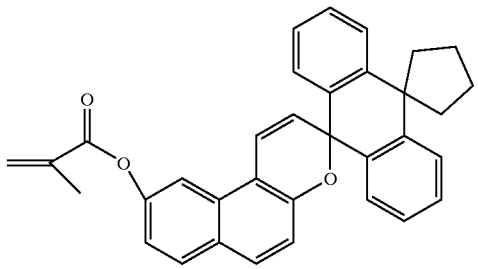

(J)

-continued

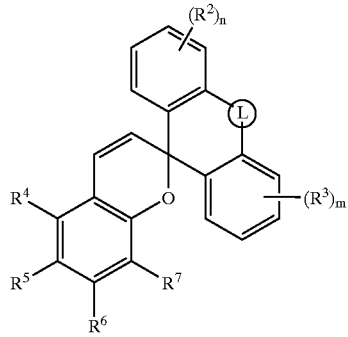

It is to the Applicant's credit to have discovered these compounds, because they have truly advantageous photochromic properties. More precisely, they possess a high colorability, particularly in the red region. They are therefore suitable for combination—in total compatibility and complementarity—with photochromic compounds absorbing in the blue, to give a wide coverage of the visible absorption spectrum and hence tints of brown or dark gray coloration.

Both their sensitivity and the height and area of their $\lambda_{max}$ peaks in the visible attain values which are more than respectable.

These compounds are furthermore perfectly stable and compatible with substrate matrices made of organic polymer or inorganic material, either in the form of an inclusion in the matrix or in the form or a coating.

In solution or in a polymeric matrix, the compounds according to the invention are colorless or slightly colored in the initial state (i.e. when not exposed to the activating radiation cause the opening of the pyran ring) and rapidly develop an intense coloration under UV light (365 nm) or under a solar type of light source. Finally, they rapidly revert to their initial color when the irradiation ceases.

The compounds of the invention can be obtained by condensing an aromatic alcohol with a propargyl alcohol. The propargyl alcohol is itself obtained by reacting an acetylide with a ketone, followed by hydrolysis. This synthetic route for the preparation of pyran rings is well known to those skilled in the art and is described for example in U.S. Pat. No. 5,238,981. The scheme for synthesizing the compounds according to the invention is shown below.

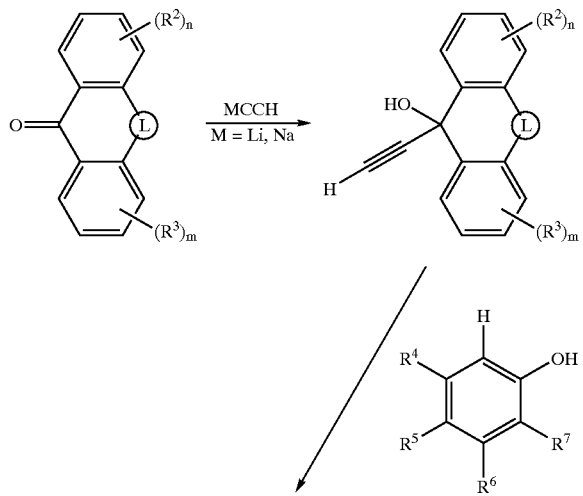

The propargyl alcohol is synthesized using e.g. either lithium acetylide (preferably in the form of a diamine complex) or sodium acetylide (suspended in paraffin oil) in an appropriate solvent such as tetrahydrofuran, dioxane, toluene, dimethyl sulfoxide, dimethylformamide or an ether. The reaction with the ketone takes place at a temperature between −78° C. and +150° C. The progress of the reaction is monitored chromatographically on a silica or alumina plate.

The condensation reaction of the propargyl alcohol with the aromatic alcohol is carried out in a solvent such as tetrahydrofuran, dioxane, toluene, benzene or ethanol, in the presence of an acid catalyst such as paratoluenesulfonic acid, sulfiuric acid, chloroacetic acid or acidic alumina. The stoichiometry of the reactants, the reaction temperature and the reaction time depend on the reactivity of the propargyl alcohol and the aromatic alcohol. These conditions are optimized to give a good yield. Typically the reaction time can vary from 1 hour to a few days and the temperature from 0° C. to 100° C. Another synthetic route, also applicable to some compounds of the invention, is described in patent application EP 0 562 915.

As far as the applications the compounds according to the present invention are concerned, it should be noted that they can be used as photochromic substances in solution or on and/or in a polymeric or inorganic matrix.

A photochromic solution can be obtained by solubilizing the compound in an organic solvent such as toluene, dichloromethane, tetrahydrofuran or ethanol. The solutions obtained are generally colorless and transparent. When exposed to sunlight, they develop a strong coloration and revert to the colorless state when they are placed in a zone less exposed to the solar radiation or, in other words, when they are no longer subjected to UV. In general, very little product (of the order of 0.01 to 5%) suffices to give an intense coloration.

The most common applications are those in which the photochromic compound is uniformly dispersed in or on the surface of a polymer, copolymer or mixture of polymers. A very wide variety of procedures can be considered. An example which may be mentioned among the procedures known to those skilled in the art is diffuision into the (co)polymer from a suspension or solution of the photochromic compound in a silicone oil, in an aliphatic or aromatic hydrocarbon, in a glycol or in another polymeric matrix. The diffiusion is commonly effected at a temperature of 50 to 200° C. for a period of 15 minutes to a few hours, depending on the nature of the polymeric matrix.

Another practical technique consists in mixing the photochromic compound with a formulation of polymerizable substances, depositing this mixture on a surface or in a mold and then performing the polymerization.

Other practical techniques within the scope of those skilled in the art are described in the article by CRANO et al. entitled "Spiroxazines and their use in photochromic lenses", published in "Applied Photochromic Polymer Systems" by Blackie and Son Ltd—1992.

In one variant of the invention, it is also possible to consider grafting the photochromic compounds onto (co) polymers. Thus another subject of the invention is formed by the (co)polymers onto which at least one of the photochromic compounds described above has been grafted.

The following products may be mentioned as examples of preferred polymeric materials for optical applications of the photochromic compounds according to the invention:

polyalkyl, polycycloalkyl, polyaryl or polyarylalkyl mono-, di-, tri- or tetra-acrylate or -methacrylate which is optionally halogenated or contains at least one ether and/or ester and/or carbonate and/or carbamate and/or thiocarbamate and/or urea and/or amide group, polystyrene, polycarbonate (e.g. polybisphenol-A carbonate, polyallyl diethylene glycol carbonate), polyepoxy, polyurethane, polythiourethane, polysiloxane, polyacrylonitrile, polyamide, aliphatic or aromatic polyester, polyvinyl, cellulose acetate, cellulose triacetate, cellulose acetate-propionate or polyvinylbutyral, copolymers of two or more types of monomers or mixtures of polymers mentioned above, preferably polycarbonate/polyurethane, poly(meth)acrylate/polyurethane, polystyrene/poly(meth)acrylate or polystyrene/polyacrylonitrile, advantageously a mixture of polyester and polycarbonate or poly(meth) acrylate.

The amount of photochromic compound used depends on the desired degree of darkening. In general, the amount used is between 0.01 and 20% by weight, based on the total weight of the polymeric matrix.

The photochromic compounds according to the invention can be used by themselves or in a mixture with other products to form a composition which can be in the solid or liquid form, for example in solution or in dispersion, as already mentioned above. These compositions, which constitute a further subject of the invention, can therefore comprise the compounds (I), (I') of the invention and other complementary photochromic compounds, making it possible to obtain the dark gray or brown colorations which the public desires in applications such as sunglasses. These complementary photochromic compounds have a L and an absorption surface in the visible which are such that, after association with the spiropyrans of the invention, an absorption spectrum is obtained which covers the whole of the visible and imparts the desired tint to the mixture of activated photochromic compounds.

The photochromic compound or compounds which can be associated with the compounds of the invention are for example the ones known to those skilled in the art and described in the literature, namely spirooxazines (J. C. CRANO et al.—"Applied Photochromic Polymer Systems"—published by Blackie & Son Ltd–1992, chapter 2), chromenes (U.S. Pat. No. 3,567,605, EP 0 562 915), spiropyrans or naphthospiropyrans (U.S. Pat. No. 5,238, 981).

These compositions according to the invention can also contain:

non-photochromic colorants for adjusting the tint, and/or one or more stabilizers, for example an antioxidant, and/or one or more UV inhibitors, and/or one or more free radical inhibitors, and/or one or more deactivators of photochemical excited states.

The durability of said compositions can be improved by these additives.

POSSIBILITY OF INDUSTRIAL APPLICATION

According to another of its features relating to the application of the photochromic compounds (I) and (I'), the present invention further relates to the ophthalmic articles, such as the ophthalmic glasses or sunglasses, which comprise at least one of said compounds defined above, and/or at least one (co)polymer at least partially formed of repeat units of the type (I) or (I'), and/or at least one composition comprising the compounds (I) and (I') according to the invention, as defined above, and/or at least one matrix, as defined above, made of an organic polymeric material, an inorganic material or an inorganic/organic hybrid material.

In practice, the articles to which the present invention relates more particularly are photochromic ophthalmic lenses, glazing [windows for buildings and locomotive devices (motor vehicle)], optical devices such as decorative articles, articles for solar protection, etc.

The present invention will be understood more clearly with the aid of the following Examples of the synthesis and photochromic validation of the compounds (I) and (I') to which it relates. These Examples also reveal all the advantages and practical variants of the present invention.

EXAMPLES

SYNTHESIS AND PROPERTIES OF PHOTOCHROMIC COMPOUNDS (A) TO (J) ACCORDING TO THE INVENTION (EXAMPLES 1 TO 10)

The results and formulae are collated in Table 1 below.

TABLE 1

LEGEND:
* λ<sub>max</sub> measured at 0.1% in tetrahydrofuran, exposed to a 60,000 Lux xenon lamp, at a temperature of 20–25° C. and with 3 mm thick matrix films,
* IOD = induced optical density at saturation,
* Stability = photochemical stability assessed by measurement of the IOD at saturation after 4 hours of photochemical ageing.

| PHOTOCHROMIC COMPOUND | | $\lambda_{max}$ (nm) | IOD | Stability (IOD) |
|---|---|---|---|---|
| A(Ex. 1) | [structure] | 444 | 0.93 | 0.93 |
| B(Ex. 2) | [structure] | 485 | 1.02 | 0.63 |
| C(Ex. 3) | [structure] | 444 | 1.20 | 1.10 |
| D(Ex. 4) | [structure] | 480 | 1.10 | 0.90 |

TABLE 1-continued

LEGEND:
* λ$_{max}$ measured at 0.1% in tetrahydrofuran, exposed to a 60,000 Lux xenon lamp, at a temperature of 20–25° C. and with 3 mm thick matrix films,
* IOD = induced optical density at saturation,
* Stability = photochemical stability assessed by measurement of the IOD at saturation after 4 hours of photochemical ageing.

| PHOTOCHROMIC COMPOUND | λ$_{max}$ (nm) | IOD | Stability (IOD) |
|---|---|---|---|
| E(Ex. 5) | 480 | 1.10 | 0.90 |
| F(Ex. 6) | 486 | 0.61 | 0.60 |
| G(Ex. 7) | 458 | 1.13 | 1.11 |
| H(Ex. 8) | — | — | — |

TABLE 1-continued

LEGEND:
* λ$_{max}$ measured at 0.1% in tetrahydrofuran, exposed to a 60,000 Lux xenon lamp, at a temperature of 20–25° C. and with 3 mm thick matrix films,
* IOD = induced optical density at saturation,
* Stability = photochemical stability assessed by measurement of the IOD at saturation after 4 hours of photochemical ageing.

| PHOTOCHROMIC COMPOUND | λ$_{max}$ (nm) | IOD | Stability (IOD) |
|---|---|---|---|
| I(Ex. 9) | 480 | 1.37 | 1.35 |
| J(Ex. 10) | 442 | 0.26 | — |
| Kc | 450 | 1.00 | 0.00 |
| Mc | 428 | 1.1 | — |

TABLE 1-continued

LEGEND:
* λ$_{max}$ measured at 0.1% in tetrahydrofuran, exposed to a 60,000 Lux xenon lamp, at a temperature of 20–25° C. and with 3 mm thick matrix films,
* IOD = induced optical density at saturation,
* Stability = photochemical stability assessed by measurement of the IOD at saturation after 4 hours of photochemical ageing.

| | PHOTOCHROMIC COMPOUND | λ$_{max}$ (nm) | IOD | Stability (IOD) |
|---|---|---|---|---|
| Nc | [structure] | 520 | <0.2 | — |

Example 1

Synthesis of the Compound A

LiCCH.NH$_2$C$_2$H$_2$NH$_2$ (9 g) are added in small portions, over a period of 3 hours, to a solution of 10,10-dimethylanthrone (7.5 g) in 40 ml of tetrahydrofuran, stirred at −10° C.

The mixture is then stirred at 0° C. for 2 hours. It is subsequently poured onto crushed ice. The propargyl alcohol obtained is extracted with toluene (3×400 ml). This gives a light brown solid after evaporation of the organic phase. The structure of the compound is confirmed by NMR spectroscopy. Yield: 8.3 g.

The product of the previous step (5.2 g) and 2-naphthol (3.32 g) are solubilized in 50 ml of tetrahydrofuran. A catalytic amount of p-toluenesulfonic acid is added and the mixture is kept at room temperature and under a nitrogen atmosphere for 16 h. The solution is then poured into 100 ml of water and 100 ml of diisopropyl ether. The organic phase is recovered, washed three times in 30 ml of aqueous sodium hydroxide solution (1 N) and then reduced to dryness. The product obtained (4.45 g) is recrystallized from a heptane/diisopropyl ether solvent mixture. Yield: 2.7 g. Its structure is confirmed by NMR spectroscopy.

Example 2

Synthesis of the Compound B 7 g of the propargyl alcohol of Example 1, 8.8 g of 2,6-dihydroxynaphthalene and a catalytic amount of para-toluenesulfonic acid are solubilized in 125 ml of tetrahydrofuran in a 100 ml reactor and the mixture is kept at room temperature for 2 hours. It is subsequently poured into 100 ml of water, after which 100 ml of methylene chloride are added. The organic phase is recovered and then reduced to dryness. Chromatography on a silica column with a toluenedichloromethane eluent gives the "hydroxylated" intermediate with a yield of 25%. This is then methylated with dimethyl sulfate in acetone, in the presence of potassium carbonate. The desired product (B) is obtained, after purification, in the form of a yellowish powder with a yield of 75%. Its structure is confirmed by NMR spectroscopy.

Example 3

Synthesis of the Compound C 10 g of anthrone, 5 g of LiOMe and 16 g of diiodobutane are mixed with 100 ml of xylene in a 250 ml reactor and the reaction mixture is refluxed for 16 h. It is then poured into 100 ml of water and 200 ml of toluene. The organic phase is extracted, washed with aqueous KOH solution and then reduced to dryness. The solid obtained is macerated in 100 ml of heptane and then filtered off and dried to give 9 g of spirocyclopentylanthrone. The propargyl alcohol of the latter is obtained, as in Example 1, by reaction with lithium acetylide in tetrahydrofuran at −10° C.

The compound (C) is then obtained, in a manner analogous to that described in Example 1, from the propargyl alcohol of spirocyclopentylanthrone and 2-naphthol. The product (C) is isolated in the form of a cream-colored powder with a yield of 18% and its structure is confirmed by NMR spectroscopy.

Example 4

Synthesis of the Compound D

The compound (D) is obtained, in a manner analogous to that described in Example 1, from the propargyl alcohol of spirocyclopentylanthrone (Example 3) and 2-hydroxy-6-methoxynaphthalene. The product (D) is isolated in the form of a pinkish powder with a yield of 14% and its structure is confirmed by NMR spectroscopy.

Example 5

Synthesis of the Compound E

The compound (E) is obtained, in a manner analogous to that described in Example 1, from the propargyl alcohol of spirocyclopentylanthrone and 2-hydroxy-6-p-methoxyphenylnaphthalene. The product (E) is isolated in the form of a yellowish powder with a yield of 30% and its structure is confirmed by NMR spectroscopy.

Example 6

Synthesis of the Compound F

This compound is synthesized from 10,10-dibenzylanthrone and 2-naphthol. The procedure is similar to that of Example 1. The product is isolated in the form of a cream-colored powder and its structure is confirmed by NMR spectroscopy.

Example 7

Synthesis of the Compound G

This compound is synthesized from 5,12-naphthacenequinone and 2-naphthol. The procedure is similar to that of Example 3 (selective reduction of 5,12-naphthacene-quinone with tin and hydrochloric acid, followed by reaction with diiodobutane). The product is isolated in the form of a cream-colored powder and its structure is confirmed by NMR spectroscopy.

Example 8

Synthesis of the Compound H

This compound is synthesized from spirocyclopentylanthrone and 2-hydroxy-dibenzofuran. The product is isolated in the form of a cream-colored powder and its structure is confirmed by NMR spectroscopy.

Example 9

Synthesis of the Compound I

This compound is synthesized from spirocyclopentylanthrone and 3-methyl-1-naphthol. The product is isolated in the form of a cream-colored powder and its structure is confirmed by NMR spectroscopy.

Example 10

Synthesis of the Compound J

This compound is synthesized from spirocyclopentylanthrone and 2,7-dihydroxy-naphthalene. The hydroxylated product is then reacted with methacryloyl chloride in toluene, in the presence of triethylamine. The product is isolated in the form of a cream-colored powder and its structure is confirmed by NMR spectroscopy.

Example 11

Comparative Known Compounds Kc, Le and Mc

The compound (Kc) is spiro(9-fluorene-2'-(2H)-naphtho (2,3-b)pyran), described in patent application WO 95/00 504.

The compound (Me) is 3,3-diphenyl-3H-naphtho(2,1-B) pyran, described in patent U.S. Pat. No. 3,567,605.

The compound (Nc) is also disclosed in said patent application WO 95/00 504, as well as in the work by R. C. BERTELSON entitled "Photochromism", Ed. G. H. Brown, J. Wiley and Sons Inc., N.Y. (1971), chap. III.

APPLICATION

Example 12

Incorporation of the Compounds into a Polymetracrylate

General procedure: 5 mg of each of the compounds given in Table 2 are solubilized in tetraethoxylated bisphenol-A dimethylmethacrylate (marketed under the name DIACRYL 121 by AKZO), which also contains 20 mg of 2,2'-azobis (2-methylbutyronitrile). The solution is subsequently degassed, rendered inert with argon and then poured into a glass lens mold of diameter 8 cm and thickness 2 mm. The mold is then placed in an oven at 70° C. for 12 hours. A rigid transparent lens is obtained after demolding. Under solar-type irradiation, the glass rapidly develops an orange to red coloration (the $\lambda_{max}$ values are given in Table 2) and becomes colorless again in the dark. The photochromic characteristics are given in Table 2 below. By way of comparison, the characteristics of the compounds Mc and Nc of the prior art are also given in Table 2 below.

TABLE 2

LEGENDS:
$\lambda_{max}$ measured in D121 at a thickness of 2 mm, exposed to a 60,000 Lux xenon lamp, at 22° C.,
T0 = initial transmission (non-activated state) measured at 560 nm,
TD15 = transmission after 15 min of exposure,
TF5 = transmission after 15 min of exposure, followed by 5 min of fading in the dark.

| PHOTOCHROMIC COMPOUND | | $\lambda_{max}$ (nm) | T0% at 560 nm | TD15% at 560 nm | TF5% at 560 nm |
|---|---|---|---|---|---|
| D(Ex. 4) | 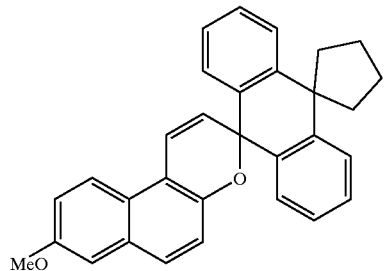 | 484 | 91 | 53 | 76 |
| G(Ex. 7) | 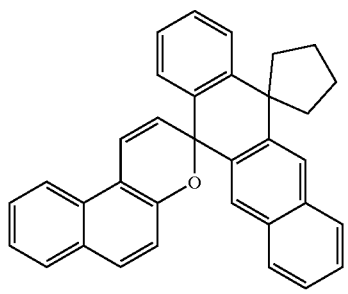 | 462 | 84 | 5 | 32 |

TABLE 2-continued

LEGENDS:

$\lambda_{max}$ measured in D121 at a thickness of 2 mm, exposed to a 60,000 Lux xenon lamp, at 22° C., T0 = initial transmission (non-activated state) measured at 560 nm, TD15 = transmission after 15 min of exposure, TF5 = transmission after 15 min of exposure, followed by 5 min of fading in the dark.

| PHOTOCHROMIC COMPOUND | $\lambda_{max}$ (nm) | T0% at 560 nm | TD15% at 560 nm | TF5% at 560 nm |
|---|---|---|---|---|
| H(Ex. 8) | 450, 545 | 89 | 76 | 84 |
| I(Ex. 9) | 488 | 87 | 28 | 37 |
| J(Ex. 10) | 447 | 91 | 87 | 89 |
| Mc(Ex. 11) | 434 | 87 | 85 | 90 |

TABLE 2-continued

LEGENDS:
$\lambda_{max}$ measured in D121 at a thickness of 2 mm, exposed to a 60,000 Lux xenon lamp, at 22° C.,
T0 = initial transmission (non-activated state) measured at 560 nm,
TD15 = transmission after 15 min of exposure,
TF5 = transmission after 15 min of exposure, followed by 5 min of fading in the dark.

| PHOTOCHROMIC COMPOUND | $\lambda_{max}$ (nm) | T0% at 560 nm | TD15% at 560 nm | TF5% at 560 nm |
|---|---|---|---|---|
| Nc(Ex. 11) 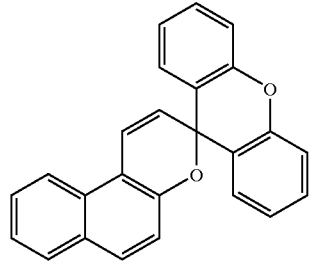 | 520 | 88 | 86 | 88 |

These measurements (Tables 1 and 2) demonstrate that the compounds of the prior art do not possess the combination of desired photochemical properties. The compound Kc is photochemically unstable, the compound Mc has a rather low $\lambda_{max}$ of the activated form and the compound Nc has a very low intensity of coloration under UV. The compound J allows grafting onto a polymer by copolymerization.

What is claimed is:

1. A compound having the following formula (I):

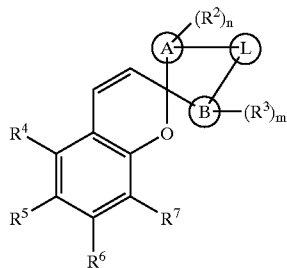

in which:
R$^2$, R$^3$, R$^4$, R$^5$, R$^6$ and R$^7$ are identical or different and are:
hydrogen,
an alkyl, cycloalkyl, alkenyl, alkynyl, aryl or heteroaryl group or an aryloxy or aralkyl group, said group optionally being halogenated,
a halogen, OR, SR, —OCOR or —COOR, where R=H, alkyl, cycloalkyl or aryl,
a polyether group, an ether group, a polyamide, an amide group, a polycarbonate group, a carbonate, a polycarbamate, a carbamate, a polyurea, a urea group, a polyester group or an ester group,
an amrino radical which—once bonded in (I)—produces a primary, secondary or tertiary amine, said amine being monosubstituted or disubstituted by alkyl, aryl or aralkyl, depending on its type,
or a cyclic or heterocyclic amino radical,
or an electron-attracting group,
n and m independently of one another take the values 0 to 4,
and wherein a bonding unit L is provided between two moieties A and B consisting of aromatic or heteroaromatic rings wherein A and B are identical or different, said bonding unit L being selected from the following group of radicals:

where:
R$^8$ and R$^9$ are identical or different and are a linear or branched C$_1$–C$_{12}$ alkyl, a C$_1$–C$_{12}$ cycloalkyl, an aralkyl or an alkylaryl,
x=1 to 3.

2. The compound according to claim 1, of the followin g formula (I'), in which A and B are phenyl groups, A=Ph$_1$, B=Ph$_2$:

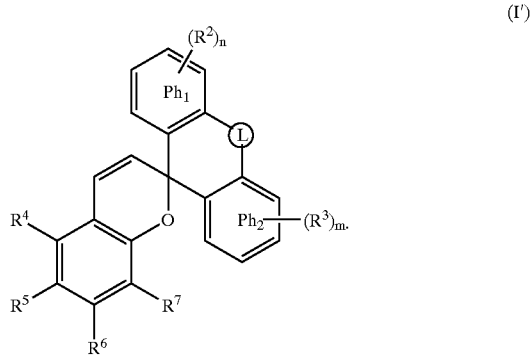

3. The compound of claim 1 wherein at least one of the groups R$^2$, R$^3$, R$^4$, R$^5$, R$^6$ and R$^7$ is a reactive polymerizing or crosslinking group; or said groups R$^2$, R$^3$, R$^4$, R$^5$, R$^6$ and R$^7$ form at least one reactive polymerizing or crosslinking group.

4. The compound of claim 1 wherein in formula (I):
R$^2$ and R$^3$ are hydrogen or —OMe,
and at least one ring formed from the radicals R$^4$ and R$^5$ or from the radicals R$^6$ and R$^7$, said ring having one of the following structures:

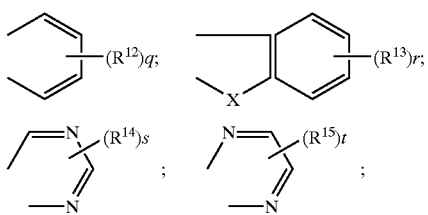
where $R^{12}$ to $R^{15}$ are defined as for $R^2$ to $R^7$ in claim 1, q, r and s=0 to 4 and t=0 to 2;
and X=O, S or N.
5. Compound according to claim 1 which consists of one of the following compounds:
(A)
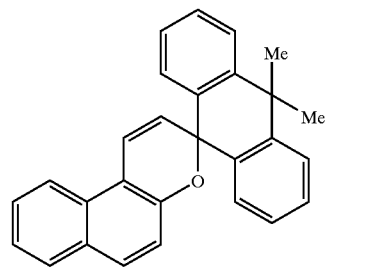
(B)
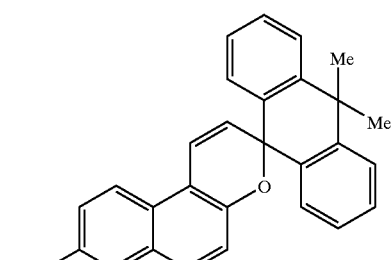
(C)
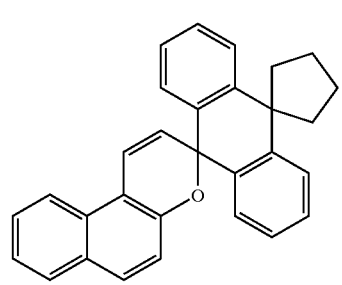
(D)
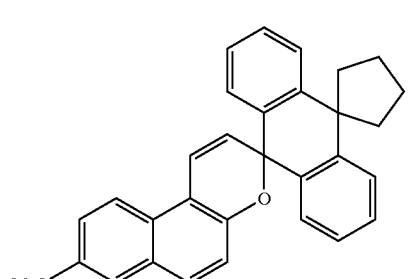
-continued
(E)
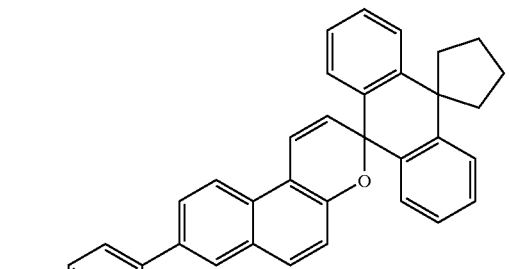
(F)
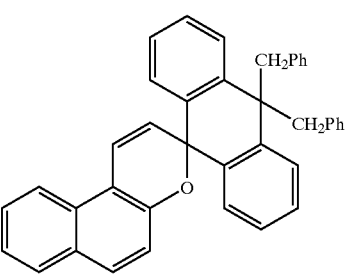
(G)
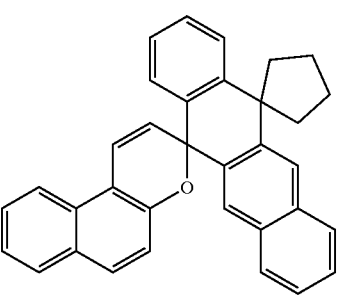
(H)
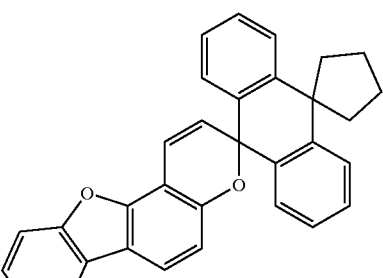
(I)
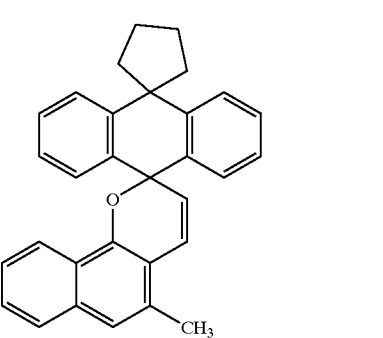

-continued

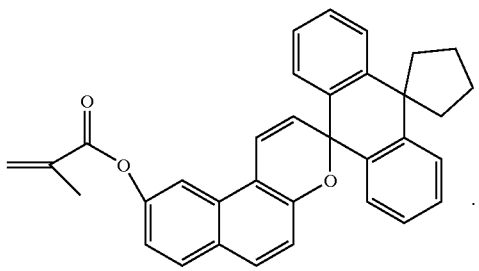

(J)

6. A (co)polymer obtained by the polymerization of at least one monomer formed by at least one photochromic compound according to claim 3.

7. A copolymer, wherein it is grafted with at least one of the photochemical compounds according to claim 1.

8. A photochromic composition, which comprises:
at least one member selected from the group consisting of a compound according to claim 1, a (co)polymer according to claim 6 and a copolymer according to claim 7,
and at least one member selected from the group consisting of colorants and stabilizers.

9. A (co)polymeric matrix, which comprises:
at least one member selected from the group consisting of a compound according to claim 1, a (co)polymer according to claim 6 and a copolymer according to claim 7,
together with at least one photochromic composition according to claim 8.

10. The matrix of claim 9, wherein the (co)polymer is selected from the following list:
polyalkyl, polycycloalkyl, polyaryl or polyarylalkyl mono-, di-, tri- or tetra-acrylate or -methacrylate which is optionally halogenated or contains at least one member selected from the group consisting of ether, ester, carbonate, carbamate, thiocarbarnate, urea and amide,
polystyrene, polycarbonate, polyepoxy, polyurethane, polythiourethane, polysiloxane, polyacrylonitrile, polyamide, aliphatic or aromatic polyester, polyvinyl, cellulose acetate, cellulose triacetate, cellulose acetatepropionate or polyvinylbutyral,
copolymers of two or more types of monomers or mixtures of polymers mentioned above.

11. An ophthalmic article comprising:
at least one member selected from the group consisting of a compound according to claim 1, a (co)polymer according to claim 6 or 7 and a composition according to claim 8,
together with a (co)polymeric matrix according to claim 9.

12. The ophthalmic article of claim 11, which is a lens.

13. The compound of claim 1 wherein the halogen is selected from the group consisting of F, Br and Cl.

14. The compound of claim 1 wherein said electron-attracting group is selected from the group consisting of $CF_3$, CN, $NO_2$ and SCN.

15. The compound of claim 1 wherein at least two of the radicals $R^4$, $R^5$, $R^6$ and $R^7$ form at least one aromatic or aliphatic ring.

16. The compound of claim 15 wherein at least two of the radicals $R^4$, $R^5$, $R^6$ and $R^7$ which form a ring are carried by two vicinal carbons.

17. The compound of claim 15 wherein said at least one aromatic or aliphatic ring has from 4 to 7 ring members.

18. The compound of claim 15 wherein said at least one aromatic or aliphatic ring formed by said at least two of the radicals $R^4$, $R^5$, $R^6$ and $R^7$, has 5 or 6 ring members.

19. The compound of claim 15 wherein said at least one aromatic or aliphatic ring include at least one heteroatom so as to form at least one heterocyclic ring.

20. The compound of claim 19 wherein said at least one aromatic or aliphatic ring is substituted by one or more identical or different radicals $R^2$ to $R^7$ wherein radicals $R^2$ to $R^7$ are as defined in claim 1.

21. The compound of claim 1 wherein L is joined to the 2,2'-positions of the rings A and B.

22. The compound of claim 1, wherein $R^8$ and $R^9$ are identical or different and are selected from the group of radicals consisting of alkylene, phenyl and alkyl.

23. The compound of claim 22 wherein said radical is methyl or methylenephenyl.

24. The compound of claims 1 wherein $R^8$ and $R^9$ are substituted.

25. The compound of claim 1 wherein $R^8$ and $R^9$ are combined to form a substituted or unsubstituted hydrocarbon ring.

26. The compound of claim 25 wherein said ring is fused with at least one member of the group consisting of aromatic rings, heteroaromatic rings, aliphatic rings and heteroaliphatic rings.

27. The compound of claim 25 wherein said hydrocarbon ring formed from $R^8$ and $R^9$ is an aliphatic ring having from 4 to 7 ring members.

28. The compound of claim 3 wherein said reactive polymerizing or cross-linking group is selected from the group consisting of alkenyl, methacryloyl, acryloyl, acryloxyalkyl, methacryloxyalkyl and epoxy.

29. The compound of claim 28 wherein said alkenyl is vinyl.

30. The compound of claim 4 wherein at least two radicals $R^4$ and $R^5$ or $R^6$ and $R^7$ form a ring selected from the group consisting of:

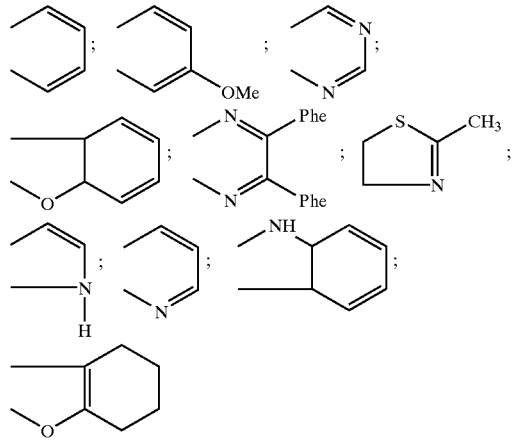

where $R^{12}$ to $R^{15}$ are defined as for $R^2$ to $R^7$ in claim 1, q, r and s 0 to 4 and t=0 to 2;
and X=O, S or N.

31. The matrix of claim 10 wherein said polycarbonate is selected from the group consisting of polybisphenol-A carbonate and polyallyl diethylene glycol carbonate.

32. The matrix of claim 10 wherein said co-polymers of two or more types of monomers or mixtures of polymers are selected from the group consisting of polycarbonate/ polyurethane, poly(meth)acrylate/polyurethane, polystyrene/poly(meth)acrylate and polystyrene/ polyacrylonitrile.

33. The matrix of claim 32 wherein said mixture of polymers is a mixture of polyester and polycarbonate or poly(meth)acrylate.

34. The ophthalmic article of claim 11 which is selected from the group consisting of ophthalmic glasses and sunglasses.

35. The compound of claim 1 with the proviso that when $R^2$, $R^3$, $R^4$, $R^5$, $RR^6$ or $R^7$ is an aryl group, said aryl group is substituted phenyl or substituted napthyl.

36. The compound of claim 2 wherein the at least one of the groups $R^2$, $R^3$, $R^4$, $R^5$, $R^6$ and $R^7$ is a reactive polymerizing or cross-linking group; or said groups $R^2$, $R^3$, $R^4$, $R^5$, $R^6$ and $R^7$ form at least one reactive polymerizing or cross-linking group.

37. The compound of claim 2 wherein in formula (I'):
$R^2$ and $R^3$ are hydrogen or —OMe,
and at least one ring formed from the radicals $R^4$ and $R^5$ or from the radicals $R^6$ and $R^7$, said ring having one of the following structures;

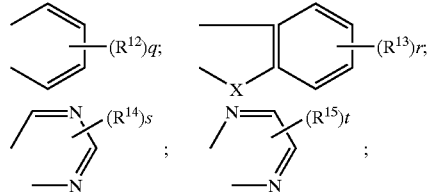

where $R^{12}$ to $R^{15}$ are defined as for $R^2$ to $R^7$ in claim 1, q, r and s=0 to 4 and t=0 to 2;
and X=O, S or N.

38. The compound according to claim 1, wherein n or m is $\geq 2$, two of the radicals $R^2$ or $R^3$ combine to form at least one aromatic ring.

* * * * *